(12) United States Patent
Fiume et al.

(10) Patent No.: US 6,291,638 B1
(45) Date of Patent: Sep. 18, 2001

(54) HEPATOTROPIC CONJUGATES OF ANTIVIRAL DRUGS CARRIERS THEREOF AND PHARMACEUTICAL COMPOSITIONS CONTAINING THEM

(75) Inventors: Luigi Fiume; Corrado Busi; Guiseppina Di Stefano; Alessandro Mattioli; Massimo Baldacci, all of Pisa (IT)

(73) Assignee: Laboratori Balducci S.p.a., Pisa (IT)

( * ) Notice: Subject to any disclaimer, the term of this patent is extended or adjusted under 35 U.S.C. 154(b) by 0 days.

(21) Appl. No.: 09/325,182

(22) Filed: Jun. 3, 1999

Related U.S. Application Data

(62) Continuation-in-part of application No. 09/053,279, filed on Apr. 1, 1998, now Pat. No. 5,959,077, which is a continuation of application No. 08/374,726, filed as application No. PCT/EP94/01702 on May 24, 1994, now abandoned.

(30) Foreign Application Priority Data

May 26, 1993 (IT) .............................. MI93A1082

(51) Int. Cl.$^7$ ...................................... A61K 38/16
(52) U.S. Cl. .............. 530/324; 530/345; 514/2; 514/12
(58) Field of Search .................. 530/324, 345; 514/2, 12

(56) References Cited

U.S. PATENT DOCUMENTS 5,959,077 * 9/1999 Fiume .................................. 530/324

OTHER PUBLICATIONS

Fiume, FEBS 203, 203–206, 1986.*
Fiume, Adv. Drug Delivery Rev. 14, 51, 1994.*
Fiume, Biochem Pharmacol 47, 643, 1994.*

\* cited by examiner

*Primary Examiner*—Christopher S. F. Low
*Assistant Examiner*—David Lukton
(74) *Attorney, Agent, or Firm*—Anderson, Kill & Olick, P.C.

(57) ABSTRACT

The present invention refers to conjugated compounds of antiviral drugs having hepatotropic activity, methods of making these compounds, and compositions thereof.

31 Claims, 7 Drawing Sheets

RETENTION TIME (MIN)
THE ARROWS 1,2,3 AND 4 INDICATE THE RETENTION TIME OF BOVINE IgG, HSA, RNAse A AND APROTININ RESPECTIVELY

HEPATOTROPIC CONJUGATES OF ANTIVIRAL DRUGS CARRIERS THEREOF AND PHARMACEUTICAL COMPOSITIONS CONTAINING THEM

This is a CIP of U.S. patent application Ser. No. 09/053,279, filed Apr. 1, 1998 now U.S. Pat. No. 5,959,077 which is a continuation of U.S. patent application Ser. No. 08/374,726, filed Mar. 17,1995, now abandoned, which is the U.S. national stage of PCT/EP94/01702, filed May 24, 1994.

BACKGROUND OF THE INVENTION

1. Field of the Invention

The present invention refers to compounds with antiviral activity and, more particularly to conjugated compounds of antiviral drugs, with carriers, having hepatotropic activity.

2. Description of the Related Art

In the treatment of the infection caused by viruses, the side effects produced by antiviral drugs can be reduced with the adoption of the chemotherapeutic lysosomotropic approach (13Balboni, P. G., Minia, A., Grossi, M. P., Barbanti-Brodano, G., Mattioli, A., Fiume, L. Activity of albumin conjugates of 5-fluorodeoxyuridine and cytosine arabinoside on poxviruses as a lysosomotropic approach to antiviral chemotherapy. Nature 1976; 264: 181–183).

This consists in conjugating the drug to a macromolecule that is selectively captured from the infected cells and transported in the lysosomes therefrom.

If, as desired, the lysosomal enzymes break the linkage between the carrier and the drug, the latter results as being concentrated in a pharmacologically active form within the infected cells.

Glossary of Terms
LAC=lactosaminated
ACVHP=acyclovir monophosphate
AZTMP=3-azido-3-deoxythymidine
ACV=acyclovir
FUDR=5-fluoro-2'-deoxyuridine
dFdC=2',2'-difluorodeoxycytidine
ASGP-R=asialoglycoprotein receptor The chronic hepatitis caused by B (HBV) virus and by C (HCV) virus are proper targets for this chemotherapeutic approach because: (a) these viruses grow especially in the hepatocytes; (b) hepatocytes specifically bring inside and transport in the lysosomes some glycoproteins with galactose residues that can therefore function as hepatotropic vectors of drugs; (c) the conjugates of drug/glycoproteins can easily come into contact with the surface of the hepatocytes inasmuch as the hepatic sinusoids are not a barrier for proteins.

Following this approach and to reduce its neurotoxic side effects, the arabinoside adenine monophosphate antiviral drug (ara-AMP), active against HBV (Jacyna, M. R., Thomas, H. C. Antiviral therapy: Hepatitis B. Brit. Med. Bull. 1990; 46: 369–382) has been conjugated with asialofetuin (AF) (Fiume, L., Mattioli, A., Busi, C., Balboni, P. G., Barbanti-Brodano, G., De Vries, J., Altman, R., Wieland, Th. Selective inhibition of Ectromelia virus DNA synthesis in hepatocytes by adenine-9-β-D-arabinofuranoside (ara-A) and adenine-β-D-arabinofuranoside 5'-monophosphate (ara-AMP) conjugated to asialofetuin. FEBS Letters 1980; 116: 185–188) and with the lactosaminated albumin (L-SA) (iume, L., Busi, C., Mattioli, A., Balboni, P. G., Barbanti-Brodano, G. Hepatocyte targeting of adenine-9-β-D-arabinofuranoside 5'-monophosphate (ara-AMP) coupled to lactosaminated albumin. FEBS Letters 1981; 129: 261–264; Fiume, L., Bassi, B., Busi, C., Mattioli, A., Spinosa, G. Drug targeting in antiviral chemotherapy. A chemically stable conjugate of 9-β-D-arabinofiranosyladenine 5'-monophosphate with lactosaminated albumin accomplishes a selective delivery of the drug to liver cells. Biochem. Pharmacol. 1986; 35: 967–972). In mice, both these two carriers have brought about a hepatic targeting of the drug.

The L-SA has a great advantage on AF: In fact, the conjugates prepared with homologous lactosaminated albumin (that is, of the same species), when introduced intravenously, do not induce the formation of antibodies (Fiume, L., Mattioli, A., Busi, C., Spinosa, G., Wieland, Th. Conjugates of adenine-9-β-D-arabinofiuranoside monophosphate (ara-AMP) with lactosaminated homologous albumin are not immunogenic in the mouse. Experientia 1982; 38: 1087–1089; Fiume, L., Busi, C., Preti, P., Spinosa, G. Conjugates of ara-AMP with lactosaminated albumin: A study on their immunogeneticity in mouse and rat. Cancer Drug Delivery 1987; 4: 145–150). In woodchuck with hepatitis by WHV (Ponzetto, A., Fiume, L., Forzani, B., Song, S. Y., Busi, C., Mattioli, A., Spinelli, C., Marinelli, M., Smedile, A. Chiaberge, E., Bonino, F., Gervasi, G. B., Rapicetta, M.,. Verme, G. Adenine arabinoside monophosphate and acyclovir monophosphate coupled to lactosaminated albumin reduce woodchuck hepatitis virus viremia at doses lower than do the unconjugated drugs. Hepatology 1991; 14: 16–24) and in patients with chronic infection by HBV (Fiume, L., Torrani Cerenzia, M. R., Bonino, F., Busi, C., Mattioli, A., Brunetto, M. R., Chiberge, E., Verme, G. Inhibition of hepatitis B virus replication by vidarabine monophosphate conjugated with lactosaminated serum albumin. Lancet 1988; 2: 13–15; Torrani Cerenzia, M. R., Fiume, L., Busi, C., Mattioli, A., Di Stefano, G., Gervasi, G. B., Brunetto, M. R., Piantino, P., Verme, G., Bonino, F. Inhibition of hepatitis B virus replication by adenine arabinoside monophosphate coupled to lactosaminated albumin. Efficacy, minimal effective dose and plasma clearance of conjugate. J. Hepatol. 1994; 20: 307–309), the ara-AMP conjugated to the L-SA has inhibited the viral replication at doses 3–6 times lower than those of the free drug.

The conjugate with L-SA should be administered intravenously owing to the high volune needed for the injection and because, by other ways antibodies are produced, and this results in poor patient compliance in long-lasting treatments.

A hepatotropic carrier of ara-AMP and of other antiviral drugs allowing the intramuscular administration of the corresponding conjugates would therefore be a remarkable improvement from the therapeutic point of view.

It is also known that a basic polyaminoacid, the poly-L-lysine, with one-third of the amino-groups substituted for galactose residues, if intravenously administered, performs a hepatic targeting of ara-AMP (Fiume, L., Bassi, B., Busi, C., Mattioli, A., Spinosa, G., Faulstich, H. Galactosylated poly (L-lysine) as a hepatotropic carrier of 9-β-D-arabinofuranosyladenine 5'-monophosphate. FEBS Letters 1986; 203: 203–206). Moreover, the poly-L-lysine, when all or large part of its ε-amino groups are substituted, does not form antibodies even when administered by ways different from the intravenous injection (Levine, B. B. Studies on antigenicity. The effect of succinylation of ε-amino groups on antigenicity of benzylpenicilloyl-poly-L-lysine conjugates in random-bred and in strain 2 Guinea pig. Proc. Soc. Exptl. Biol. Med. 1964; 116: 1127–1131; Sela, M. Immunological studies with synthetic polypeptides. Advan. Immunol. 1966; 5: 29–129).

SUMMARY OF THE INVENTION

It has now been found that if in the poly-L-lysine most of the ε-amino groups are substituted with galactose and with one of the antiviral drugs known for performing their activity against hepatic viruses, three very important therapeutic effects are produced in mice:

(i) the conjugate loses the poly-L-lysine high toxicity which distinguished the previous galactosylated poly-L-lysine-ara-AMP conjugates (Fiume et al., FEBS Letters 1986; 203: 203–206) in which most the ε-amino groups remained unsubstituted;

(ii) the antiviral drug hepatic targeting is brought on even if the conjugate is not administered intravenously and, particularly, by intramuscular injection;

(iii) the repeated conjugate administration by intramuscular and intravenous injection does not produce antibodies.

The therapeutic importance of this property will be evident if it is considered that the possibility to achieve the hepatic targeting by intramuscular injection not only involves utilizing its interesting peculiar characteristics already previously mentioned in relation to the lysosomotropic approach (i.e., drastic reduction of the side effects relevant to the toxicity of the antiviral drugs), but also equally important to make it much more comfortable for the patient to undergo the chemotherapeutic treatment which, as a rule in the viral chronic hepatitis, is long lasting.

A further object of the present invention is represented by a conjugate of a basic polyaminoacid wherein more than 50% of the side chain amino groups (the ε-amino groups) are substituted with galactose or lactose residues and drug residues and wherein said drug residues are not those of an antiviral drug, but those of an antitumoral drug. The preferred drugs are selected from 5-fluoro-2'-deoxyuridine (FUDR) and 2',2'-difluorodeoxycytidine (dFdC).

In a preferred embodiment the percentage of the side chain amino groups substituted with galactose or lactose residues is higher than or equal to 5%, whereas the percentage of those substituted with the antitumoral drug residues is higher than 30%, preferably higher than 50%.

These conjugates can be useful in the treatment of those human hepatocarcinomas which maintain the asialoglycoprotein receptor (ASGP-R) (Hyodo, I., Mizuno, M., Yamada, G., Tsuji, T. Distribution of asialoglycoprotein receptor in human hepatocellular carcinoma. Liver 1993; 13: 80–85). In a recent study the receptor was detected in 80% of the well differentiated forms of this tumor (Treré, D., Fiume, L., Badiali De Giorgi, L., Di Stefano, G., Migaldi, M., Derenzini, M. The asialoglycoprotein receptor in human hepatocellular carcinoma. Its expression on proliferating cells. Br. J. Cancer, in press).

Also, the conjugates of the present invention with an antitumoral drug show a very high water-solubility; consequently, hepatocarcinomas can now be treated by simple intramuscular, parenteral, intravenous or subcutaneous administration of water solutions containing the conjugates according to the present invention with remarkable and unobvious advantages over the traditional treatment.

Following are the results of experiments on the effect of FUDR and dFdC conjugates on a human hepatocarcinoma cell line which expresses the ASGP-R (Hep G2 cells) (Schwartz, A. L., Fridovich, S. E., Knowles, B. B., Lodish, H. F. Characterization of the asialoglycoprotein receptor in a continuous hepatoma line. J. Biol. Chem. 1981; 256: 8878–8881) and on the organ distribution in mice of [$^3$H] FUDR administered in the free form or as a lactosaminated poly-L-lysine conjugate.

In the preferred definition, the basic polyaminoacid is selected between poly-L-lysine and poly-L-ornithine and the drugs among those known from their activity against the hepatic viruses, and particularly among ara-AMP, acyclovir, ribavnin, azidothymidine, and the like.

The present invention refers therefore to the use, as carrier of antiviral drugs, of a basic, galactosylated polyaminoacid, said polyaminoacid being characterized in that most of the amino groups are substituted with molecules of the drug and with galactose molecules.

This high degree of substitution eliminates the acute toxicity of both the basic polyaminoacids and the conjugates of poly-L-lysine previously published (Fiume et al. FEBS Letters 1986; 203: 203–206) in which less than 50% of ε-amino groups were substituted by the drug and by the galactosyl residues.

The preparation of the conjugated compounds according to the present invention provides a two-step procedure:

(a) conjugation of the basic polyaminoacid with antiviral drug or with galactose residues and (b) subsequent conjugation of the conjugate resulting from step (a) with galactose residues or antiviral drug residues, respectively. In the previous general definition it can be noticed that the two conjugation steps may be inverted.

As a rule, the choice is suggested by the polyaminoacid molecular weight in a sense that, with lower molecular weights, it is preferred to carry out first the conjugation with the drug and the conjugation with galactose thereafter.

DESCRIPTION OF THE PREFERRED EMBODIMENTS

In a preferred embodiment of the process according to the present invention the drug conjugation is carried out in a way known by itself through the imidazolate of the antiviral drug in its monophosphate form and by performing the conjugation at alkaline pH (Fiume, L., Busi, C., Di Stefano, G., Mattioli, A. Coupling of antiviral nucleoside analogs to lactosaminated human albumin by using the imidazolides of their phosphoric esters. Analyt. Biochem. 1993; 212: 407–411).

The galactose residues are preferably conjugated (step b) by reductive lactosamination in the presence of sodium cyanoborohydride (Schwartz, B. A., Gray, G. R. Proteins containing reductively aminated disaccharides. Synthesis and chemical characterization. Arch. Biochem. Biophys. 1977; 181: 542–549).

As a nonlimiting example, the examples of preparation related to the use of poly-L-lysine and of poly-L-ornithine as a carrier, and of ara-AMP, acyclovir, ribavirin, and azidothymidine as antiviral drugs are reported, being understood that similar procedures are followed for preparing conjugates with other known antiviral drugs.

Conjugates with both low and high molecular weight basic polyaminoacids have been prepared.

I. Low Molecular Weight Conjugates

A. Conjugates with Poly-L-lysine

A. 1. Preparation

In a commercial composition (Sigma) of poly-L-lysine with a molecular weight of 1000–4000 Da and with an average polymerization grade of 14, the polymers with a molecular weight lower than 1800 were removed by means of gel filtration on a P2 Bio Gel column eluted with 0.2 M NH$_4$HCO$_3$. The polymers excluded from the column, after lyophilization, have been utilized to prepare the compounds shown in the following Table 1.

In all the conjugates the galactose residues have been linked to the ε-amino groups by reductive lactosamination in the present of sodium cyanoborohydride (Schwartz, B. A., Gray, G. R. Arch. Biochem. Biophys. 1977; 181: 542–549).

Compound 1

The poly-L-lysine has been labeled with [$^3$H] formaldehyde following the Jentoft and Dearborn method (Jentoft, N., Dearborn, D. G. Protein labeling by reductive alkylation. Methods Enzymol. 1983; 91: 570–579). The reaction mixture contained 44 µCi of [$^3$H]formaldehyde/ml. The [$^3$H]poly-L-lysine has been isolated by means of gel filtration on a P2 Bio Gel column and subsequent lyophilization.

TABLE 1

Characteristics of Low Molecular Weight Poly-L-Lysine Conjugates

| Compounds | µg lactose mg compound | µg drug mg compound | % ε-NH$_2$ groups substituted by Lactose | % ε-NH$_2$ groups substituted by Drug | Specific activity (dmpx 10$^3$/mg) |
|---|---|---|---|---|---|
| 1) [$^3$H]poly-L-lysine | 0 | 0 | 0 | 0 | 1,200 |
| 2) [$^{14}$C]Lac-poly-L-lysine | 721 | 0 | 92 | 0 | 860 |
| 3) [$^{14}$C]Lac-poly-L-lysine | 540 | 206 | 72 | 28 | 500 |
| 4) Lac-poly-Lysine-ara-AMP | 493 | 240 | 66 | 33 | 0 |
| 5) Lac-[$^3$H]poly-L-lysine-ara-AMP | 573 | 147 | 72 | 20 | 36,000 |
| 6) Lac-poly-L-lysine-ara-[$^3$H]AMP | 613 | 176 | 73 | 22 | 7,500 |
| 7) Lac-poly-L-lysine-[$^3$H]ACVMP | 638 | 81 | 80 | 12 | 440 |

Compound 2

The galactose has been linked to polylysine by reductive lactosamination in the presence of sodium cyanoborohydride. 20 mg of poly-L-lysine were dissolved in 2 ml of a 0.1 M boric acid/borax buffer (pH 8.5). 80 mg of alpha-lactose, containing 50 µCi of [D-glucose-1-$^{14}$C]lactose (Amersham), and 50 mg of NaBH$_3$CN have been added. The mixture has been incubated at 37° C. for 48 hours and the [$^{14}$C]Lac-poly-L-lysine isolated as for the Compound 1. The lactose contents was measured with the Dubois et al. method (Dubois, M., Gilles, K. A., Hamilton, J. K, Rebers, P. A., Smith, F. Colorimetric method for determination of sugar and related substances. Anal. Chem. 1956; 28: 350–356) and referred to the dry weight of the compound.

Compounds 3 and 4

The ara-AMP has been conjugated by means of its imidazolate (Fiume, L., Busi, C., Di Stefano, G., Mattioli, A. Analyt. Biochem. 1993; 212: 407–411).

This procedure is more effective than that employing the water-soluble carbodiimides and avoids the chemical side reactions produced by these substances.

The ara-AMP imidazolate has been prepared with the Lohrmann and Orgel method (Lohrmann, R., Orgel, L. E. Preferential formation of (2'-5')-linked internucleotide bonds in non-enzymatic reactions. Tetrahedron 1978; 34: 853–855). Poly-L-lysine was dissolved (50 mg/ml) in a 0.1 M NaHCO$_3$/Na$_2$CO$_3$ buffer, pH 9.5. After the addition of the ara-AMP imidazolate (75 mg/ml), the pH was readjusted at 9.5 with HCl and the mixture incubated for 48 hours at 37° C. The conjugates have been isolated as the Compound 1; the ara-AMP content was determined spectrophotometrically and referred to the dry weight of the conjugates, which were further lactosaminated (for Compound 4 using unlabeled lactose).

Compound 5

The poly-L-lysine/ara-AMP conjugate, obtained as indicated for Compounds 3 and 4, has been labeled with [$^3$H]formaldehyde (100 mCi/mmole).

The reaction mixture contained 2,800 µCi [$^3$H] formaldehyde/ml. The labeled conjugate has been then lactosaminated as described above. This conjugate was used as antigen in determining the antibodies with the Minden and Farr method (Minden, P., Farr, R. S. The ammonium sulphate method to measure antigen-binding capacity, Weir, D. M. ed. Handbook of Experimental Immunology, Blackwell, Oxford 1973; 15.1–15.21).

Compound 6

The conjugation of tritiated ara-AMP in this compound was performed using 1-ethyl-3-(dimethyl aminopropyl) carbodiimide (ECDI), since the ara-[$^3$H]AMP conversion in its imidazolate causes an almost complete loss of tritium. The poly-L-lysine was first lactosaminated as described above (Compound 2), but reducing the reaction period from 48 to 24 hours in order to to substitute with the sugar only two-thirds of the ε-amino groups.

Afterward, the ara-[$^3$H]AMP was conjugated according to the above procedure (Fiume, L., Bassi, B., Busi, C., Mattioli, A., Spinosa, G., Faultstich, H. FEBS Letters 1986; 203: 203–206). In the preparation of this conjugate the first step was the lactosamination to reduce the number of the free ε-amino groups at the time of use of the ECDI and, therefore the possibility of polymerizing the poly-L-lysine molecules by means of this compound.

Compound 7

The [$^3$H]ACVMP employed to produce this conjugate was obtained by phosphorylation (Yoshikawa, M., Kato, T., Takenishi, T. A novel method for phosphorylation of nucleosides to 5'-nucleotides. Tetrahedron Letters 1967; 50: 5065–5068) of [$^3$H]ACV(triziate at the position 2 of the side chain) (NEN). The conjugate was prepared as for Compounds 3 and 4, with the difference that the incubation of the poly-L-lysine with imidazolated [$^3$H]ACVMP lasted only 6 hours. The [$^3$H]ACVMP imidazolate was made with the above-cited Lohrmann and Orgel method.

The conjugated product of this invention obtained in the previous examples underwent chemical/physical determinations and biological tests aimed at finding the experimental confirmation of the therapeutical properties of the compounds themselves.

BRIEF DESCRIPTION OF THE DRAWINGS

The following determinations are referred to in the enclosed figures in which.

A.2. Experimental Observations (a) Average Molecular Weight of Compound 4

Figure 1:
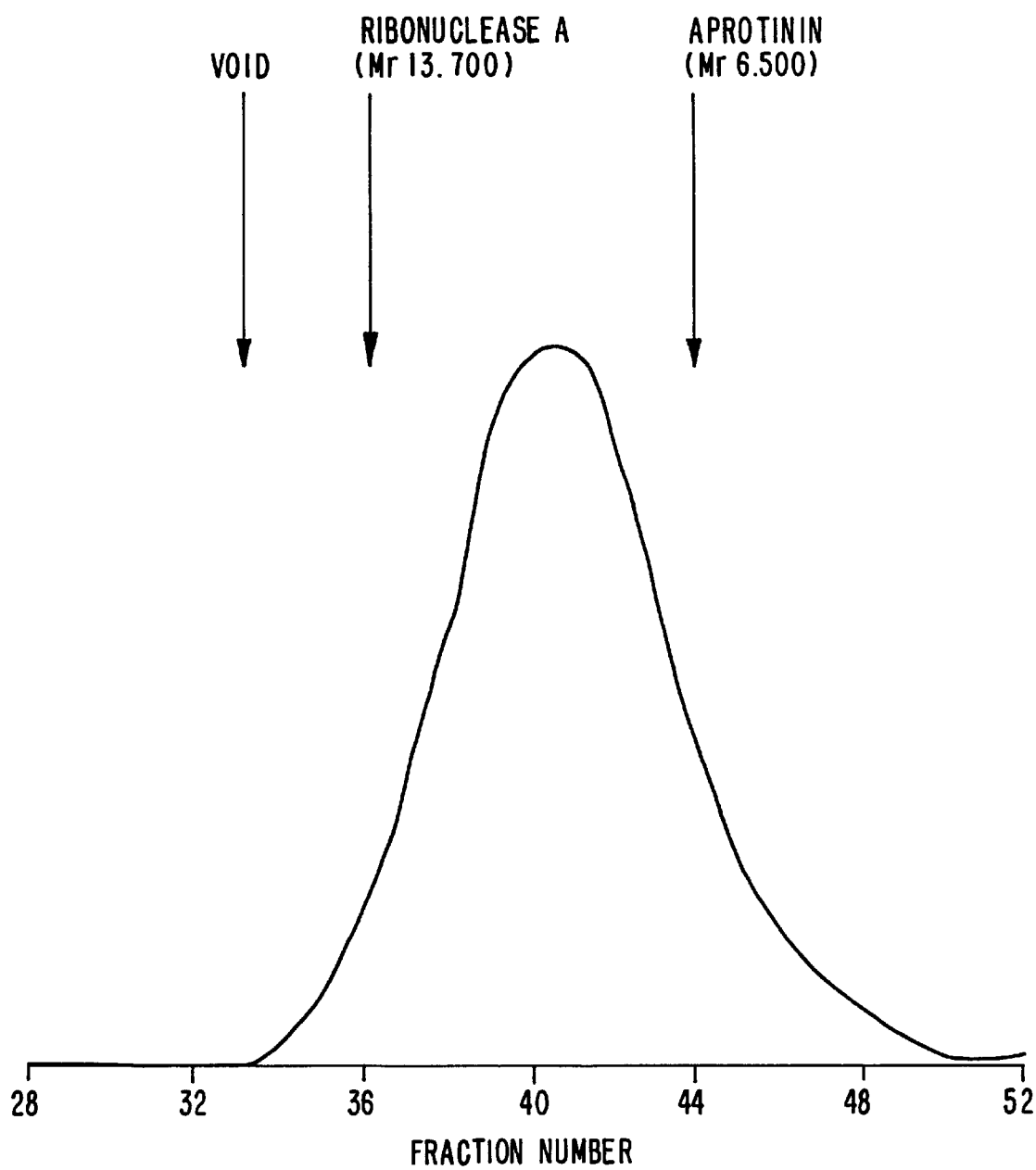
FIG. 1 shows the chromatographic diagram on Bio Gel P 10 of the Lac-poly-L-lysine-ara-AMP (Compound 4 of Table 1).

FIG. 1 shows the chromatography of the Lac-poly-L-lysine-ara-AMP (Compound 4 of Table 1) on a Bio Gel P 10 (1.6×92) column calibrated with dextran blue 2000 (void volume), ribonuclease (Mr 13,700) and aprotinin (Mr 6,500).

25 mg of conjugate were loaded on a 1.6×92 cm column equilibrated and eluted 0.2 M with NH$_4$HCO$_3$. The fractions were of 2 ml. The elution volumes both of the conjugate and the markers (the latter indicated by arrows) were determined.

With the Whitaker method (Whitaker, J. R. Determination of molecular weights of proteins by gel filtration on sephadex. Analyt. Chem. 1963; 35: 1950–1953) it was calculated that the conjugate average molecular weight is 9,100 corresponding to a carrier with 19 lysine residues and an average molecular weight of 2,400.

(b) Distribution of the Compounds in the Organs

As already mentioned, FIGS. 2A through 2H show the radioactivity distribution in the mice organs after the intramuscular injection of: A, [$^3$H]poly-L-lysine (24 μg/g); B, [$^{14}$C]Lac-poly-L-lysine (24 μg/g); C, ara-[$^3$H]AMP (5 μg/g); D, [$^{14}$C]Lac-poly-L-lysine-ara-AMP (24 μg/g); E, Lac-poly-L-lysine-ara-[$^3$H]AMP (28 μg/g corresponding to 5 μg/g of ara-[$^3$H]AMP; F, [$^3$H]ACVMP (4 μg/g); G, Lac-poly-L-lysine-[$^3$H]ACVMP (50 μg/g corresponding to 4 μg/g of [$^3$H]ACVMP).

All the compounds were injected in a volume of 10 μl/animal in the leg's posterior muscles using a 25 μl Hamilton microsyringe.

The radioactivity contribution afforded by the plasma contained in the organs has been calculated (Fiume, L., Busi, C., Mattioli, A. Lactosaminated human serum albumin as hepatotropic drug carrier—Rate of uptake by mouse liver. FEBS Letters 1982; 146: 42–46) and substracted.

Each datum represents the average of results achieved on 2–3 animals.

The standard error varied from 0.1% to 2.0% of the average values.

As illustrated after admninistration of [$^3$H]poly-L-lysine (2A), ara-[$^3$H]AMP (2C) and [$^3$H]ACVMP (2F) the radioactivity quantities in liver, spleen, intestine and brain are practically equivalent. And instead, after injection of [$^{14}$C] Lac-poly-L-lysine (2B) and of the conjugates of the Lac-poly-L-lysine with ara-AMP and AGVMP, labeled in the lactose (2D) or in the drugs (2E, 2G), the radioactivity levels in liver are higher than those of the other organs.

The percentages of radioactivity measured in 1 gr of liver after ara-[$^3$H]AMP and [$^3$H]ACVMP (2C, 2F) administration are similar to those calculated after injection of an equal dose of these drugs conjugated to the Lac-poly-L-lysine (2E, 2G).

In kidneys, the radioactivity levels reach the same values as in liver one hour after the injection of the labeled conjugates (Compound 3 in Table 1) or 1.5–2 times higher (Compounds 6 and 7). In subsequent times, the radioactivity levels of kidneys are equal or lower as compared with those of liver. The high radioactivity levels in kidneys might be explained by the remark that various polypeptides, after glomerular filtration, are endocytized by the cells of kidneys proximal tubules (Maack, Th., Johnson, V., Kau, S. T., Figueiredo, J., Sigulem, D. Renal filtration, transport and metabolism of low molecular weight proteins. Kidney Int. 1979; 16: 251–270). The penetration into renal cells should not have any effect on the chemotherapic index of the Lac-poly-L-lysine/antiviral drugs conjugates. In fact, excluding acyclovir that tends to precipitate in the kidneys tubules (Balfour, H. H. Acyclovir and other chemotherapy for herpes group viral infections. Ann. Rev. Med. 1984; 35: 279–291), the antiviral nucleosides are not particularly toxic for the cell of this organ.

(c) Digestion of Compound 3 in Liver

Figure 3:
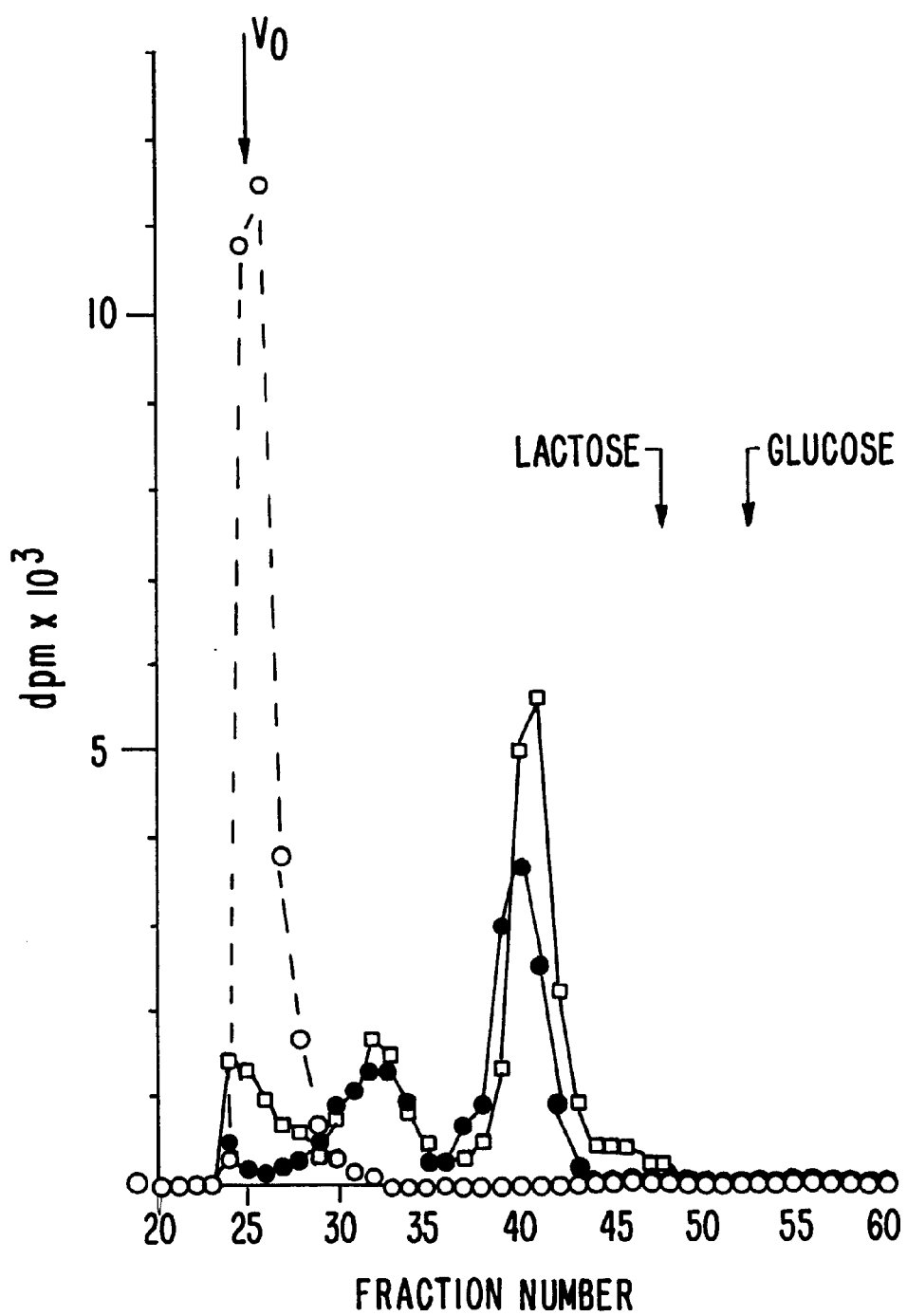
FIG. 3 shows the chromatographic diagram on Bio Gel P 2 of liver extracts of mice injected with the Compound 3 of Table 1.

The rupture of the linkage between ara-AMP and the ε-amino groups of the galactosylated poly-L-lysine within hepatic cells was demonstrated by previous researches (Fiume, L, Bassi, B., Bongini, A. Conjugates of 9-β-D-arabinofuranosyladenine 5'-monophosphate (ara-AMP) with lactosaminated albumin: Characterization of the drug-carrier bonds. Pharm. Acta Helv. 1988; 63: 137–139). FIG. 3 shows the chromatographic profiles on Bio Gel P 2 of the mice liver extracts, 2 and 6 hours after the intramuscular injection of [$^{14}$C]Lac-poly-L-lysine-ara-AMP (24 μg/g).

Female Swiss mice of 28–30 gr received by intramuscular injection the conjugate (24 μg/g in a total volume of 10 μl).

After 3 (□) or 6 (●) hours the mice were sacrificed (two animals for each time) and the livers have been homogenized with 4 volumes of cold water; 5 volumes of perchloric acid were immediately added and after centrifugation the supernatants were neutralized with KOH.

After 2 hours in the cold the potassium perchlorate was centrifuged and the supernatants freeze-dried.

The freeze-dried material has been redissolved with 2 ml of H$_2$O and, after centrifugation to clarif the solution, 1 ml was chromatographed on a Bio Gel P 2 (1.6×92 cm) column equilibrated and eluted with 0.2 M NH$_4$HCO$_3$.

The radioactivity present in the fractions, wherein molecules included in the gel and having dimensions larger than those of lactose have been eluted, demonstrates that the poly-L-lysine is fragmented in liver even though its ε-amino groups are still linked to the sugar.

The symbol ○ in the figure relates to the chromatographic profile of the extract of a homogenized liver obtained from two untreated mice and to which the conjugate (14 μg/ml) was added just before the precipitation with perchloric acid.

(d) Production of Antibodies in Mice Treated with Compound A

Twelve female Swiss mice (weight of 28–30 g at the start of the test) received the conjugate No. 4 (Table 1) administered in the posterior leg's muscles for five days a week for four weeks in succession (daily single dose=700 μg/animal in 10 μl 0.9% NaCl).

The mice were bled from the retroorbital plexus with ethereal anaesthesia a week after the last injection.

The antibodies were measured in 50 μl of serum and in triplicate by means of the precipitation method with ammonium sulphate according to the Minden and Farr procedure.

As antigen the conjugate 5 (Table 1) was used.

In the presence of 50 µl of serum of 5 untreated mice, the precipitated dpm have been 78±11 (SE). In the presence of 10 µl of a mice serum able to link either the ara-A (938 pmoles of ara-A linked by 1 ml of serum) or the ara-AMP conjugated to the L-HSA (Fiume, L., Bassi, B., Busi, C., Mattioli, A., Wieland, Th. A study on the pharmacokinetics in mouse of adenine-9-β-D-arabinofuranoside 5'-monophosphate conjugated with lactosaminated albumin. Experientia 1985; 41: 1326–1328), the precipitated dpm have been 1599±21.

In the presence of the serums of the twelve mice treated with the Lac-poly-L-lysine-ara-AMP conjugate, the precipitated dpm ranged from a minimum of 41±5 to a maximum of 80±6 dpm.

This result showed that none of the treated mice produced antibodies measurable with the employed method, the sensitivity of which was of about 0.5 µg/IgG/ml of serum.

(e) Acute Toxicity of Compound 4

The Lac-poly-L-lysine-ara-AMP conjugate (No. 4), dissolved in 0.9% NaCl, was administered to female Swiss mice of 28–30 g intravenously (5 animals) or subcutaneously (5 animals) with a single injection of 0.4 ml/animal and in a 1.3 mg/g dose.

It did not show any evidence of toxicity.

Figure 2:
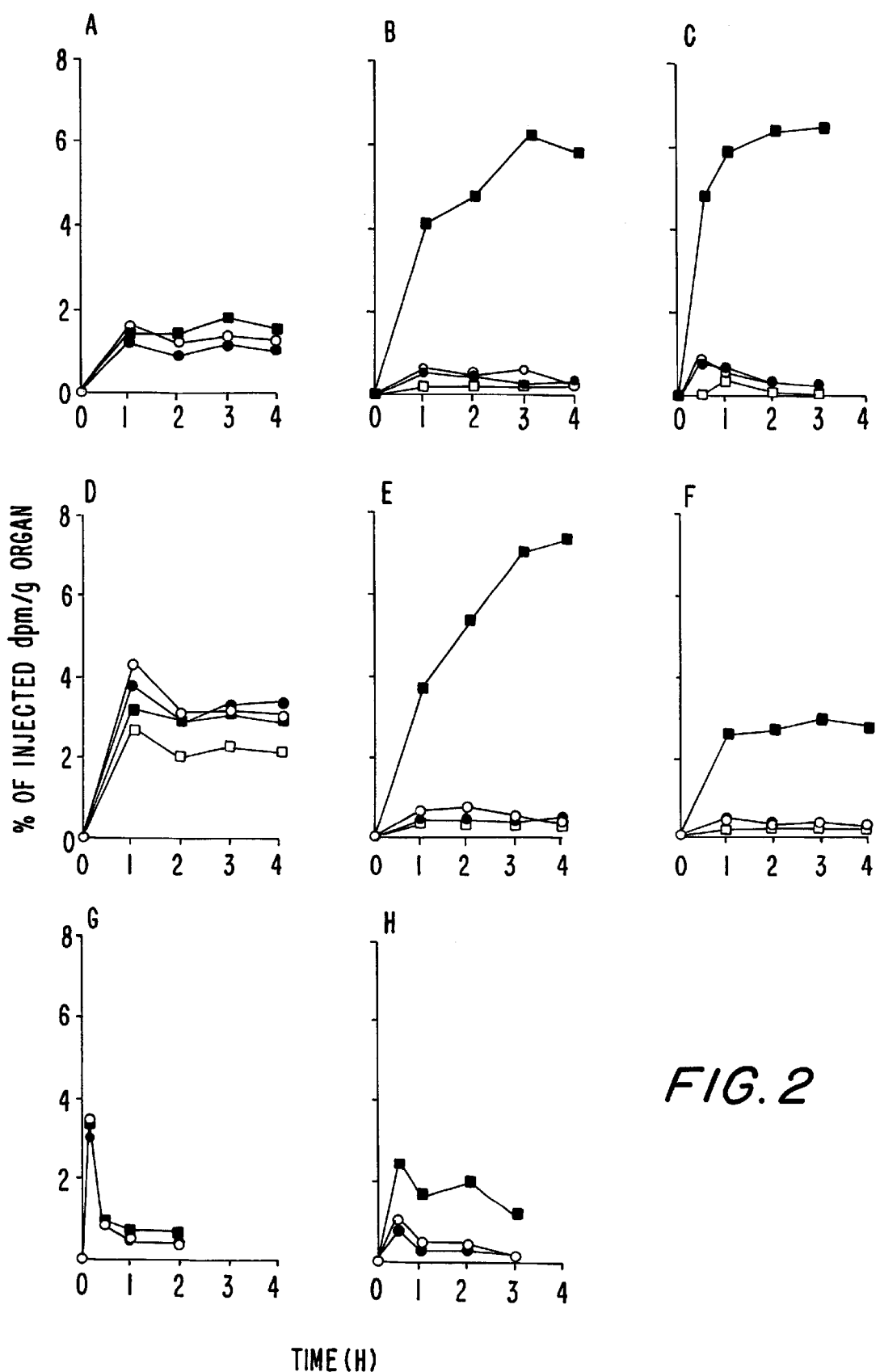
FIGS. 2A through 2H show the radioactivity distribution of liver (■), in spleen (●), in intestine (○) and in brain (□) of female Swiss mice (28–30 g) to which the compounds of the invention (Table 1) and the unconjugated compounds for comparison have been administered by intramuscular injection.

The injected dose was 50 times higher as compared with that administered by intramuscular injection in the distribution experiments of the conjugate in the organs (FIG. 2).

The $LD_{50}$ for female Swiss mice of the poly-L-lysine utilized for producing this conjugate, injected in the form of a hydrochloric acid salt intravenously, resulted to be within 30 and 60 µg/g.

(f) Solubility of the Compound 4

In patients with chronic hepatitis B the unconjugated ara-AMP is administered at 2.5 or 5 mg/kg doses with two injections a day.

The Lac-poly-L-lysine-ara-AMP (No. 4) conjugate readily dissolves in a physiological solution at the concentration of 400 mg/ml.

24 mg/kg, dose corresponding to 5 mg/kg of ara-AMP, can be therefore administered to a patient of 70 kg weight in a volume lower than 5 ml.

B. Conjugate with Poly-L-Ornithine

B.1. Preparation

Compound 8

This compound was prepared using a poly-L-ornithine HBr (Sigma) with a molecular weight of 5,300–7,600. Poly-L-ornithine (25 mg) was labeled with [$^3$H] formaldehyde (100 mCi/mmole) (NEN) according to Jentoft and Dearborn Methods Enzymol. 1983; 91: 570–579). The reaction mixture contained 98 µCi [$^3$H]formaldehyde/ml. [$^3$H]poly-L-ornithine was isolated from the reaction mixture by gel filtration on a Bio Gel P 2 column eluted with 0.5 M $NH_4HCO_3$ and was subsequently lyophilized. Ara-AMP imidazolate was coupled to the labeled polymer using the procedure followed for Compounds 3 and 4.

For subsequent lactosamination 10 mg [$^3$H]poly-L-ornithine-ara-AMP were dissolved in 1 ml 0.1 M borax/NaOH buffer, pH 10, together with 80 mg α-lactose and 50 mg $NaBH_3CN$. The solution was incubated for 72 hours at 37° C.

The lactosaminated conjugate (Lac-[$^3$H]poly-L-ornithine-ara-AMP) was recovered by gel filtration on a Bio Gel P 2 column eluted with 0.5 m $NH_4HCO_3$ and was subsequently lyophilized. 1 mg of the compound (specific activity 668 dpm/µg) contained 134 µg ara-AMP (spectrophotometrically determined) and 604 µg lactose (measured according to Dubois et al. Anal. Chem. 1956; 28: 350–356). About 90% of polymer ϵ-amino groups were substituted: 17% with the drug, 73% with lactose.

B.2. Experimental Observations (a) Organ distribution of Compound 8

Figure 4:
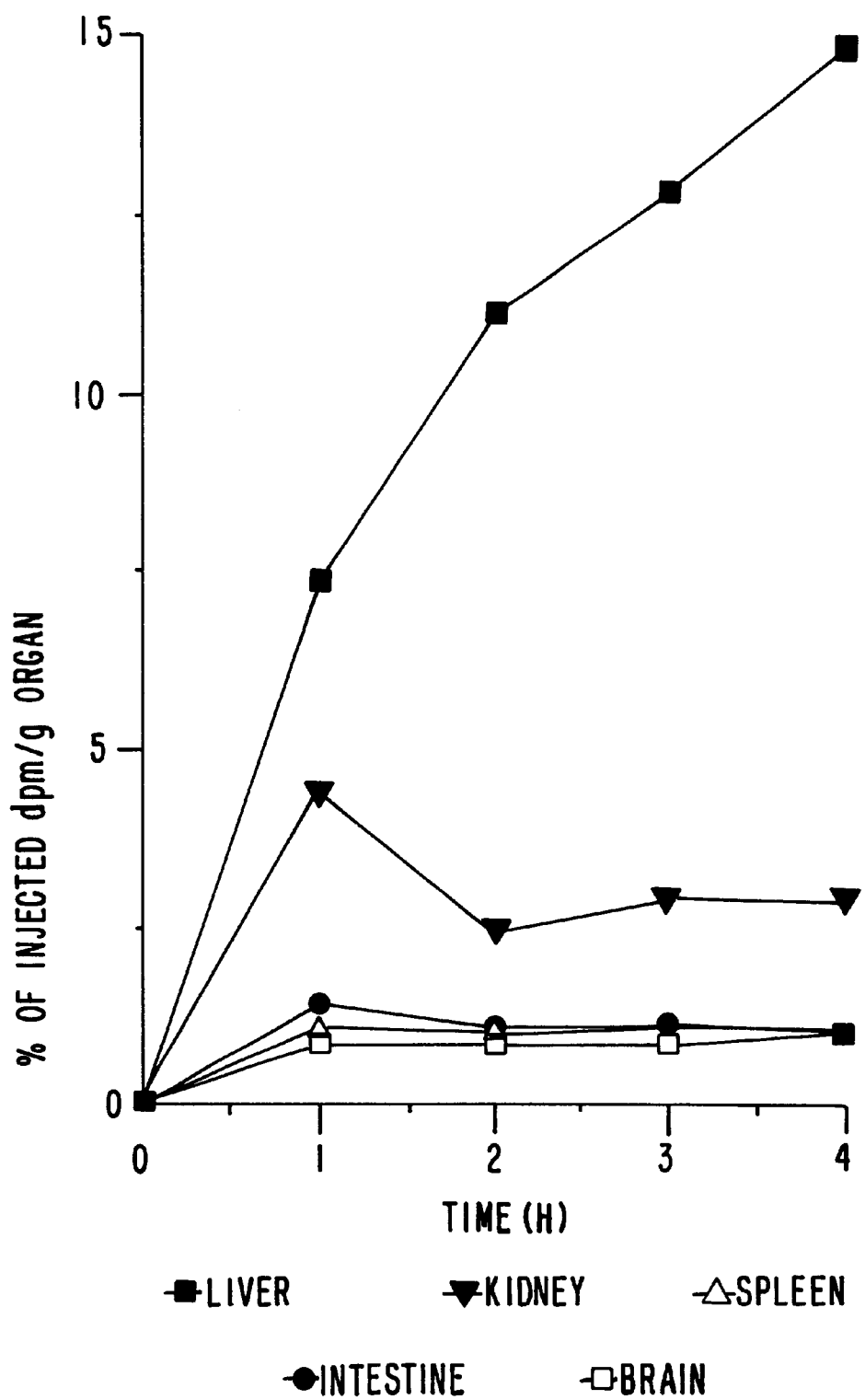
FIG. 4 shows the organ radioactivity distribution in mice after intramuscular injection of Lac-[$^3$H]poly-L-lysine-ara-AMP.

FIG. 4 shows the organ distribution of radioactivity in mice after intramuscular injection of Lac-[$^3$H]poly-L-ornithine-ara-AMP (36.5 µg/g, corresponding to 5 µg/g ara-AMP). Experimental procedure was as described for the similar experiments with the lac-poly-L-lysine conjugates. The levels of radioactivity in liver were higher than in the other organs. Radioactivity values in kidney were 3–4 times higher than in spleen, intestine and brain.

II. High Molecular Weight Conjugates

In patients with viral hepatitis the clearance of galactosyl terminating macromolecules is much slower tan in mice, rats and normal humans, probably because of a slower penetration into hepatocytes (Marshall, J. S., Williams, S., Jones, P. Serum desialylated glycoproteins in patients with hepatobiliary dysfunctions. J. Lab. Clin. Med. 1978; 92: 30–37; Torrani Cerenzia, M. R., et al. J. Hepatol. 1994; 20: 307–309). As a consequence, in these patients the renal elimination of the conjugates prepared with low molecular weight polyaminoacids is expected to be even greater than that measured in mice.

To overcome this drawback we prepared conjugates using a high molecular weight poly-L-lysine. In these conjugates also most of the ϵ-amino groups of poly-L-lysine were substituted by drug and galactose molecules.

We observed that:

(1) High molecular weight conjugates also specifically penetrate liver cells after intramuscular administration.
(2) The renal loss of these conjugates is very low and, consequently, the percentage of injected dose entering hepatocytes is higher than that measured after administration of low molecular weight conjugates.
(3) High molecular weight conjugates are also devoid of acute toxicity and, after repeated intramuscular or intravenous administration, do not induce antibodies.
(4) Due to their high solubility (more than 150 mg/ml) and heavy drug load, a pharmacologically active dose could be administered in a small volume, well compatible with the intramuscular route.

II. 1. Preparation

These conjugates were prepared using a poly-L-lysine HBr with a molecular weight of 30–70,000 and a polymerization degree of 145–335 (Sigma). As in the preparation of low molecular weight poly-L-lysine conjugates drugs were coupled via the imidazolate of their phosphoric esters and lactose was linked by reductive amination in the presence of $NaBH_3CN$. However, the procedure was modified: The pH, temperature, length of reaction time as well as the imidazolate concentration were all increased in the drug conjugation step. Moreover, lactosamination was performed before drug coupling since at high pH high molecular weight poly-L-lysine precipitated unless a part of ϵ-$NH_2$ groups were substituted with galactose residues.

Compound 9

Reductive lactosamination of ϵ-$NH_2$ groups was carried out by dissolving 200 mg poly-L-lysine in 20 ml 0.4 M potassium phosphate buffer pH 7, together with 800 mg α-lactose and 500 mg $NaBH_3CN$. After incubation at 37° C. for 24 hours the pH was raised to 8 with 5 M KOH and the solution was left at 37° C. for a further 6 hours.

Lac-poly-L-lysine was diafiltered with 0.9% NaCl and concentrated to 100 mg/ml. Lactose was measured by the phenol-sulfuric acid method of Dubois et al. (Anal. Chem.

1956; 28: 350–356) using galactose as a standard; poly-L-lysine was determined by measuring the nitrogen according to Kjeldahl. 2 ml Lac-poly-L-lysine solution (=200 mg) were diluted with 2 ml 1 M sodium carbonate buffer, pH 11. 800 mg ara-AMP imidazolate, synthesized according to Lohrmann and Orgel (Tetrahedron 1978; 34: 853–855), were dissolved and the pH was readjusted to 11 with 5 M NaOH.

After incubation at 50° C. for 96 h, the conjugate was diafiltered with 0.9% NaCl. Chemical characterization of the complex was performed by assaying the coupled drug spectrophotometrically and by measuring lactose as described. The interference of ara-AMP in the colorimetric analysis was subtracted. The poly-L-lysine content of conjugate was calculated from the amount of lactose, knowing the weight ratio lactose/poly-L-lysine determined before drug coupling (see above). This was possible because the bond between the sugar and lysine $\epsilon$-$NH_2$ groups did not break down during drug conjugation, as we verified experimentally. The conjugate was concentrated in saline (0.9% NaCl) to 150 mg/ml and lyophilized after freezing to about −80° C. The concentration of conjugate was calculated without taling account of contraions.

Prior to use, Lac-poly-L-lysine-ara-AMP was dissolved with water at the concentration of 150 mg/ml. It easily dissolved provided the freezing was rapid. When necessary, the conjugate was diluted with 0.9% NaCl.

Compound 10

Prior to coupling with ara-AMP, Lac-poly-L-lysine was labeled with [$^3H$]formaldehyde (NEN) according to Jentoft and Dearborn (Methods Enzymol. 1983; 91: 570–579). The reaction mixture contained 78 $\mu$Ci [$^3H$]formaldehyde/ml. After diafiltration with 0.9% NaCl Lac-[$^3H$]poly-L-lysine was conjugated with ara-AMP as described above.

Compound 11

Ribavirin (RIBV) (1-$\beta$-D-ribofuranosyl-1,2,4-triazole-3-carboxamide) was first phosphorylated (RIBVMP) accord to (Allen, L. B., Boswell, K. H., Khwaja, T. A., Meyer, R.B., Sidwell, R. W., Witkowski, J. T. Synthesis and antiviral activity of some phosphates of the broad-spectrum antiviral nucleoside, 1-$\beta$-D-Ribofuranosyl-1,2,4-triazole-3-carboxamide (Ribavirin). J. Med. Chem. 1978; 21: 742–746).

The pyridinium salt of the phosphorylated derivative was then converted to the imidazolate (Lohrmann and Orgel, Tetrahedron 1978; 34: 853–855), which was coupled to Lac [$^3H$]poly-L-lysine as described for the conjugate with ara-AMP. In this conjugate coupled RIBVMP was assayed by measuring the organic phosphate according to (Ames, B. N. Assay of inorganic phosphate. Total phosphate and phosphatases. Methods Enzymol. 1966; 8: 115–118).

Due to the strong interference of RIBV with the colorimetric assay of sugar, we could not measure lactose as described for Lac-poly-L-lysine-ara-AMP and therefore we determined Lac-[$^3H$]poly-L-lysine content of the conjugate by counting the radioactivity.

Compound 12

3'-azido-3-[2-$^{14}C$]deoxythymidine ([$^{14}C$]AZT) (Moravek) was phosphorylated according to Yoshikawa et al. (Tetrahedron Letters 1967; 50: 5065–5068). The pyzidinium salt of the phosphorylated derivative was converted to its imidazolate and subsequently coupled to Lac-poly-L-lysine. Coupling was performed as described for Compound 9, but in the reaction medium the ratio of the amount of drug imidazolate to that of the polymer was 2.7 instead of 4. The chemical characterization of this conjugate was performed as described for Compound 9.

Compound 13

This conjugate was prepared as Compound 9, but lactosamination of poly-L-lysine was interrupted after the first 24 hours. Moreover, the ratio of the amount of ara-AMP imidazolate to that of the polymer was 4.6 instead of 4.0 30% of the $\epsilon$-amino groups of the polymer was substituted with galactosyl residues and 64% with ara-AMP.

II.2. Experimental Observations (a) Average Molecular Weights of Compound 9

Figure 5:
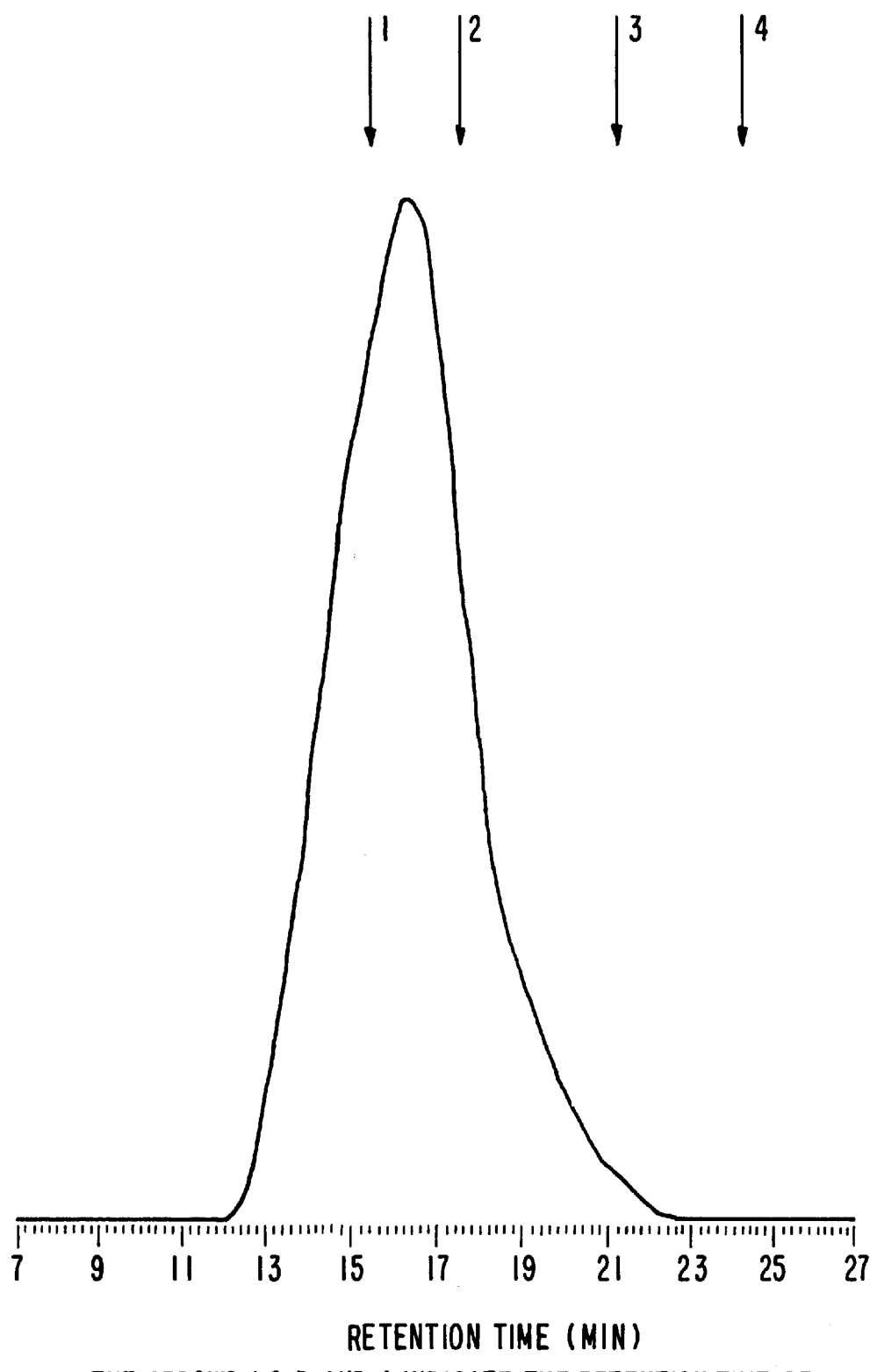
FIG. 5 shows the gel permeation chromatography of Compound 5.

They were determined by permeation chromatography using HPLC equipment (Waters) with two Protein-Pak columns 125 and 300 SW) connected in series. Compound 9 (80 $\mu$g) was dissolved in 20 $\mu$l mobile phase (125 mM $Na_2SO_4$+2 mM $NaH_2PO_4H_2O$, to pH 6.0 with 0.1 N NaOH, filtered and degassed) and chromatographed with the following conditions. Flow rate: 0.9 ml/min; detection: UV at 260 nm, 0.1 absorbance units per full scale (AUFS). Columns were calibrated with aprotinin (Mr 6,500), RNAse (Mr 13,700), HSA (Mr 69,000) and IgG (Mr 158,000). Weight average molecular weight and number average molecular weight were determined using the GPC 745/745B Waters Software. They were found to be 140,339 and 72,419, respectively. The gel permeation chromatography of Compound 9 is shown in FIG. 5.

(b) Organ Distribution of Compounds

Experimental procedure was as described for the similar experiments with low molecular weight conjugates. Results are shown in FIG. 6.

Conjugates of ara-AMP and RIBVMP were radioactive in the carrier whereas the conjugate of AZTMP was labeled in the drug moiety.

After i.m. administration of the conjugates labeled in the carrier (FIG. 6, Frames A, C) radioactivity was high in liver and low in spleen, intestine and kidney. The percentages of injected dpm recovered in kidneys were 10–20 times lower than those measured after i.m. administration of the complexes prepared with low molecular weight poly-L-lysine. Since renal accumulation of proteins is a consequence of their glomerular filtration (Maack, Th., Johnson, V., Kau, S. T., Figuereido, J., Sigulem, D. Renal filtration, transport, and metabolism of low-molecular weight proteins: A review. Kidney Int. 1979; 16: 251–270), the present result indicates that, as expected, only small amounts of the high molecular weight conjugates passed through the glomeruli at least after i.m. administration (see below).

Figure 6:
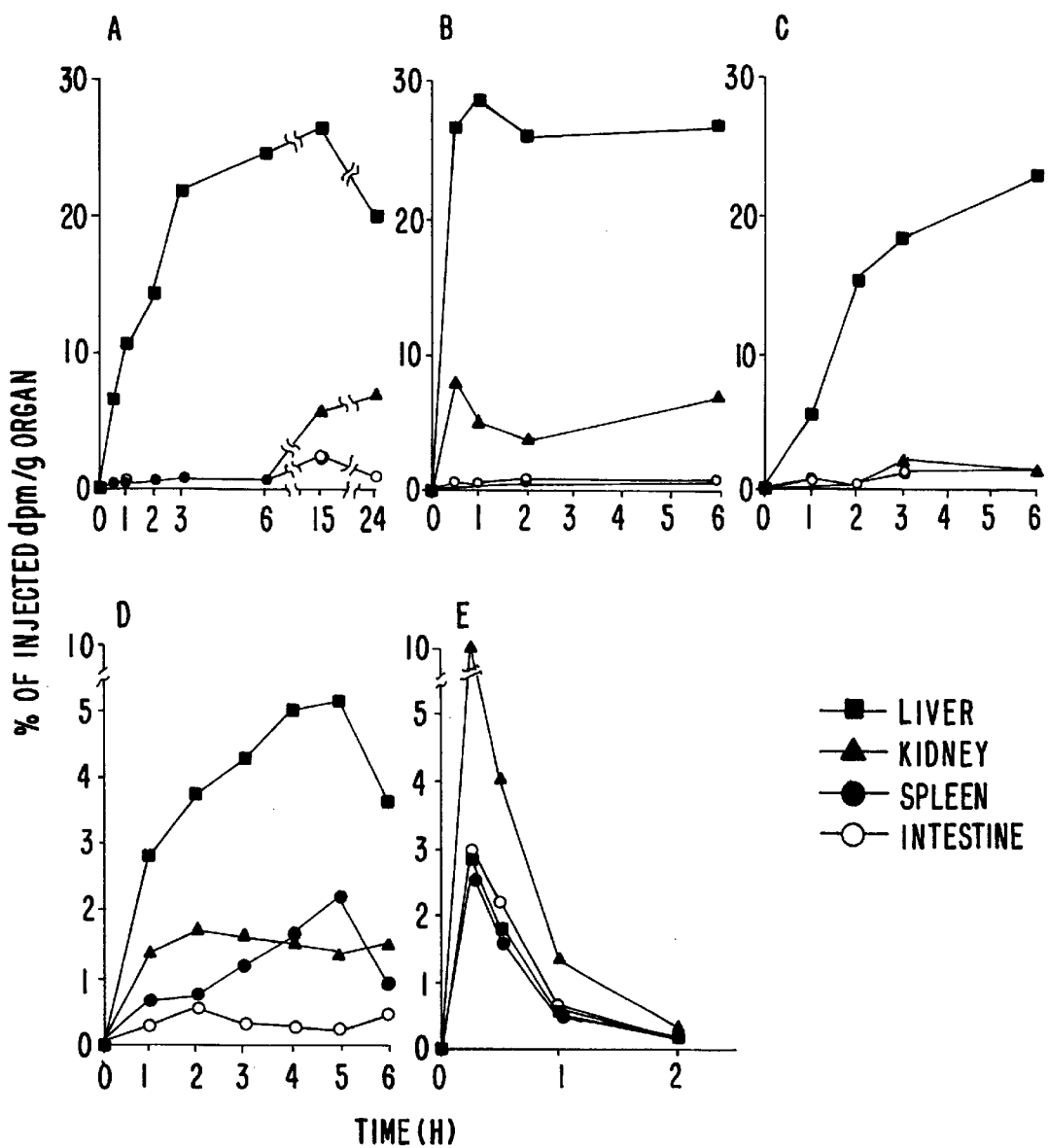
FIGS. 6A through 6E show the organ distribution of compounds having low molecular weight conjugates.

In mice i.m. injected with Lac-poly-L-lysine-[$^{14}C$] AZTMP the level of radioactivity in liver was from 2.5 to 6 times higher than in kidneys, spleen and intestine (FIG. 6, Frame D). The difference between the amount of radioactivity in liver and in other organs was less marked than that in animals administered with the conjugates labeled in the carrier (FIG. 6, Frames A, C). This result was probably due to a partial release of the drug (and/or its metabolites) from liver cells into the bloodstream after the intracellular cleavage of the drug-carrier bond. A similar release of the drug from hepatic cells in bloodstream was observed after administration of other drug/carrier hepatotropic conjugates (Fiume, L., Busi, C., Corzani, S., Di Stefano, G., Gervasi, G. B., Mattioli, A. Organ distribution of a conjugate of adenine arabinoside monophosphate with lactosaminated albumin in the rat. J. Hepatol. 1994, in press; Fiume, L., Mattioli, A., Balboni, P. G., Tognon, M., Barbanti-Brodano, G., De Vries, J., Wieland, Th. Enhanced inhibition of virus DNA synthesis in hepatocytes by trifluorothymidine coupled to asialofetuin. FEBS Letters 1979; 103: 47–51).

When free [$^{14}C$]AZTWP was i.m. injected into mice the radioactivity was equally distributed in liver, spleen and intestine with higher values in kidneys (FIG. 6, Frame E).

The rate of accumulation and decline of radioactivity after administration of free or coupled [$^{14}$C]AZTAP was different. After injection of the free drug, radioactivity accumulated in tissues within the first 15 min and then rapidly declined; after injection of the conjugated drug radioactivity in liver increased up to 4–5 h. At 1–2 hours the amounts of radioactivity in liver were bigher in animals injected with conjugated [$^{14}$C]AZTMP at the dose of 2 μg/g than in those administered with the free drug at 5 μg/g.

In mice injected intravenously with Lac-[$^3$H]poly-L-lysine-ara-AMP (FIG. 6, Frame B) the conjugate rapidly accumulated in liver; in these animals the values of radioactivity in kidneys were higher than in those which i.m. received the same conjugate (FIG. 6, Frame A). This can be explained considering that:

(i) part of conjugate molecules had a molecular weight lower than that of HSA (FIG. 5)1

(ii) a direct relationship exists between plasma concentration and glomerular filtration of small proteins (Maack, Th. et al. Kidney Int. 1979; 16: 251–270);

(iii) the concentrations of conjugate in plasma which were constantly low (less than 0.9 μg/ml) following the i.m. administration reached high values after the intravenous injection (104 μg/ml at 3 min).

(c) Experiments of Tolerability and Immunogenicity

They were performed using Compound 9. The conjugate administered intravenously (i.v.) to 5 mice at the dose of 1.5 g/Kg did not cause any recognizable sign of suffering. 1.5 g of Lac-poly-L-lysine-ara-AMP contained 480 mg of drug (see Table 2), a dose 300 times higher than that at which ara-AMP, when conjugated to L-HSA, inhibits virus growth in HBV-infected patients. In mice the LD$_{50}$ of poly-L-lysine used for preparing the conjugate, given i.v. as salt of HCl, was between 15 and 30 mg/Kg. To study whether Lac-poly-L-lysine-ara-AMP dissolved in saline at the concentration of 150 mg/ml can damage the tissues at the site of administration, a primary eye irritation expernment was performed in 6 rabbits by placing 0.1 ml of the solution in the conjunctival sac. No eye changes were observed in any animal.

Semithin sections of liver from mice and rats which received Lac-poly-L-lysine-ara-AMP administered with different schedules (see Table 3) were observed with a light microscope. In none of the animals were changes found in either parenchymal or sinusoidal liver cells. Accumulation into secondary lysomes of noncompletely digested molecules (disaccharides, peptides) which cannot cross lysosomal membrane results in a rapid swelling of these organeles which at light microscope appear as cytoplasmic vacuoles. Such vacuoles were observed in hepatic cells of mice and rats 24 h after a single administration of L-HSA-ara-AMP at doses 5–10 times higher than that active in HBV-infected patients (Fiume, L., Betts, C. M., Busi, C., Corzani, S., Derenzini, M., Di Stefano, G., Mattioli, A. The pathogenesis of vacuoles produced in rat and mouse liver cells by a conjugate of adenine arabinoside monophosphate with lactosaminated albumin. J. Hepatol. 1992; 15: 314–322). The absence of vacuoles in liver cells of mice and rats after administration of high doses of Lac-poly-L-lysine-ara-AMP gave indirect evidence of a rapid digestion of this conjugate into products able to cross the lysosomal membrane.

To study the immunogenicity of Lac-poly-L-lysine-ara-AMP twenty-four mice received the conjugate for five days a week for four consecutive weeks (single daily dose=200 μg/animal). Twelve mice were intramuscularly injected while the others were administered intravenously. A week after the last injection mice were bled and antibodies against the conjugate were measured as described for low molecular weight conjugates. None of the animals produced antibodies in amounts detectable by our assay (sensitivity about 0.5 μg IgG/ml serum).

From the previous experimental data it appears as most likely proved that the antiviral nucleosides galatosylated poly-L-lysine conjugates, in which most of the ε-amino groups of the bomopolymer are substituted by the galactose residues and the drugs, administered by intramuscular injection, perform a hepatic targeting of drugs without producing antibodies.

They do not possess the acute toxicity of poly-L-lysine used for their preparation. In comparison with conjugates with the lactosaminated albumin, that need to be injected intravenously since they are otherwise immunogenic, the conjugates provided with the galactosylated poly-L-lysine are potentially able, in the infection by hepatic viruses, to improve the patient compliance with a prolonged administration of the antiviral agent.

As already mentioned, the foregoing referred to the conjugates wherein the carrier was poly-L-lysine or poly-L-ornithine; the experimentally verified chemical-physical properties and biological behavior make acceptable the identical use as carriers of the other polyaminoacids.

These other conjugates fall therefore within the scope of the invention, as well as the employment of such polyaminoacids as carriers for preparing hepatotropic conjugates with antiviral compounds the administration of which would be otherwise seriously compromised by unfavorable side phenomena induced by a high toxicity for organs other than liver.

TABLE 2

Characteristics of High Molecular Weight Poly-L-Lysine Conjugates

| Compounds | Lactose (μg) Compound (mg) | Drug (μg) Compound (mg) | % ε-NH$_2$ groups substituted by Lactose | Drug | (dpm/μg) |
|---|---|---|---|---|---|
| 9) Lac-poly-L-lysine-ara-AMP | 385 | 330 | 48 | 43 | 0 |
| 10) Lac-[$^3$H]poly-L-lysine-ara-AMP | 352 | 312 | 44 | 41 | 2,910 |
| 11) Lac-[$^3$H]poly-L-lysine-RIBVMP | 396 | 299 | 46 | 39 | 2,504 |
| 12) Lac-poly-L-lysine-[$^{14}$C]AZTMP | 371 | 219 | 45 | 26 | 466 |
| 13) Lac-poly-Lysine-ara-AMP | 210 | 440 | 31 | 64 | 0 |

TABLE 3

Schedules of Administration of Lac-poly(L-Lys)-ara-AMP
to Mice and Rats for the Microscopic Study of Liver Cells

| Animal | Daily Dose (µg/g) | Route of Injection | Days of Administration |
|---|---|---|---|
| Mice | 6 | i.m. | 20 |
|  | 30 | i.v. | 1 |
|  | 60 | i.v. | 1 |
| Rats | 6 | i.m. | 7 |
|  | 30 | i.m. | 7 |
|  | 60 | i.v. | 1 |

Animals were killed 24 h after the last injection. Liver samples were fixed and semithin sections were stained as described in (Fiume, L., Betts, M. C., Busi, C., Corzani, S., Dernzini, M., Di Stefano, G., Mattioli, A. J. Hepatol. 1992; 15: 314–322).

III. Anititumoral Conjugates

A. Material and Methods

Poly-L-lysine HBr with an average molecular weight of 35 kDa corresponding to 168 lysine residues) was purchased from Sigma (St. Louis, Mo., USA). Coupling of lactose was performed by reductive lactosamination. Coupling of maltose was performed using the same procedure of reductive amination (Schwartz, B. A., Gray, G. R. Proteins containing reductively animated disaccharides. Synthesis and chemical characterization. Arch. Biochem. Biophys 1977;181: 542–549). The conjugate with maltose (M-poly(LYS)-FUDR) was prepared in order to have a control FUDR conjugate without galactose or lactose residues. FUDR and dFdC were conjugated by means of their imidazolates (Di Stefano, G., Busi, C., Mattioli, A., Fiume, L. Selective delivery to the liver of antiviral nucleoside analogs coupled to a high molecular mass lactosaminated poly-L-lysine and administered to mice by intramuscular route. Biochem. Pharmacol. 1995; 49: 1769–1775). The reaction conditions as well as the procedure for determining the amount of sugar and of the drug are the same as disclosed in the previous examples. In preparing the [$^3$H]FUDR conjugate, pH and temperature were decreased to the values of 9.5 and 37° C., respectively, in order to avoid a substantial loss of tritium; however, the drug load of this conjugate was found not to be reduced (Table 4).

Experiments in vitro were performed using Hep G2 cells, which were grown in Minimum Essential Medium supplemented with nonessential aminoacids, 10% foetal calf serum, 2 mM L-glutamine, 1 mM sodium pyruvate, 20 mM tricine buffer, 100 IU/ml penicillin, 100 µg/ml streptomycin. Before experiments, 7×10$^5$ cells, suspended in 2 ml of culture medium, were seeded into each well of a 6-well Nunclon multidish plate (PBI International, Milan, Italy). After 24 hours, compounds were added and cells from four wells were harvested and counted. Each dose of compounds was tested in quadruplicate. After a further 24 hours, cells from treated cultures and from four untreated wells were separately harvested and counted and the increase in cell number during the period in which the compounds were present were calculated.

For the experiments on organ distribution of free and conjugated [$^3$H]FUDR, Swiss female mice weighing 28–30 g were used. The compounds, dissolved in NaCl 0.9%, were injected into the back muscles of the right hind leg in a volume of 10 µl per animal. At different times, mice were anaesthetized with ether; liver, intestine and heart were rapidly removed and homogenized in 4 vol. (wt/vol) of water. Mice died while under anaesthesia; total radioactivity of liver, intestine and heart was measured as described (Fiume, L., Di Stefano, G., Busi, C., Mattioli, A., Rapicetta, M., Giuseppetti, R., Ciccaglione, A. R., Argentini, C. Inhibition of woodchuck hepatitis virus replication by adenine arabinoside monophosphate coupled to lactosaminated poly-L-lysine and administered by intramuscular route. Hepatology 1995; 22: 1072–1077).

B. Results

B.1. Experiments with L-poly(LYS)-FUDR

The chemical characteristics of FUDR conjugates of L-poly(LYS) and M-poly(LYS) are reported in Table 4.

TABLE 4

Chemical Characteristics of the Conjugates

| Conjugate | Sugar (µg) ÷ Conjugate (mg) | FUDR (µg) ÷ Conjugate (mg) | % ε-NH$_2$ groups substituted by: Sugar | % ε-NH$_2$ groups substituted by: Drug |
|---|---|---|---|---|
| L-poly(LYS)-FUDR | 237 | 340 | 29 | 57 |
| L-poly(Lys)-[$^3$H]FUDR[b] | 213 | 366 | 26 | 63 |
| M-poly(LYS)-FUDR | 149 | 430 | 20 | 80 |

The stability of the bond between FUDR and L-poly(LYS) in blood was measured by determining the percentage of radioactivity released from L-poly-(LYS)-[$^3$H]FUDR when the conjugate was incubated up to 6 hours at 37° C. in mouse, rat or human blood. The bond was completely stable in human blood whereas 3% and 5% of the drug was released from the carrier after 6 h incubation in rat and mouse blood respectively. L-poly-(LYS)-[$^3$H]FUDR, incubated at 37° C. for 24 hours in a medium in which Hep G2 cells have been cultured for 3 days, released only 4% of the drug. Table 5 shows that, at a concentration of 0.3 µg/ml, L-poly-(LYS)-[$^3$H]FUDR completely inhibited Hep G2 cell proliferation (Exp. 2). Inhibition was rescued by thymidine and by asialofetuin (Exp. 4 and 5) and was not produced by M-poly(LYS)-FUDR, which lacks the galactosyl residues (Exp. 3). Taken together these results demonstrate that L-poly-(LYS)-FUDR entered into Hep G2 cells through the asialoglycoprotein receptor and after intracellular penetration released FUDR in a pharmacologically active form.

TABLE 5

Effect of Free and Conjugated FUDR on Hep G2 Cell Proliferation

| Exp. | Compounds | Concentration µg/ml | Number of formed cells × 10$^5$ |
|---|---|---|---|
| 1 | Control |  | 2.4 ± 1.0 |
|  | FUDR | 0.1 | 0 |
|  | FUDR | 0.05 | 0 |
|  | FUDR | 0.01 | 0.3 ± 0.2 p = 0.046 |
|  | FUDR | 0.005 | 0.7 ± 0.3 NS[b] |
|  | FUDR | 0.001 | 2.6 ± 0.6 NS |
| 2 | Control |  | 2.5 ± 1.0 |
|  | L-Poly(LYS)-FUDR | 0.6 (0.22)[a] | 0 |
|  | L-Poly(LYS)-FUDR | 0.3 (0.11) | 0 |
|  | L-Poly(LYS)-FUDR | 0.06 (0.02) | 0.2 ± 0.1 p = 0.044 |
|  | L-Poly(LYS)-FUDR | 0.03 (0.01) | 1.1 ± 0.2 NS |
| 3 | Control |  | 3.6 ± 1.2 |
|  | L-Poly(LYS)-FUDR | 0.6 (0.22) | 0 |
|  | M-Poly(LYS)-FUDR | 1.0 (0.5) | 3.3 ± 0.6 NS |
| 4 | Control |  | 2.6 ± 1.0 |
|  | L-Poly(LYS)-FUDR | 0.3 (0.11) | 0 |
|  | L-Poly(LYS)-FUDR + thymidine | 0.3 (0.11) 10 | 2.4 ± 0.2 NS |
| 5 | Control |  | 3.1 ± 0.7 |

TABLE 5-continued

Effect of Free and Conjugated FUDR on Hep G2 Cell Proliferation

| Exp. | Compounds | Concentration μg/ml | Number of formed cells × $10^5$ |
|---|---|---|---|
| | L-Poly(LYS)-FUDR | 0.3 (0.11) | 0 |
| | Asialofetuin | 1,000 | 2.9 ± 0.2 NS |
| | L-Poly(LYS)-FUDR + asialofetuin | 0.3 (0.11) 1,000 | 2.0 ± 0.5 NS |

[a] The amounts of FUDR contained in the conjugates are shown in brackets.
[b] NS = not significant.

Figure 7:
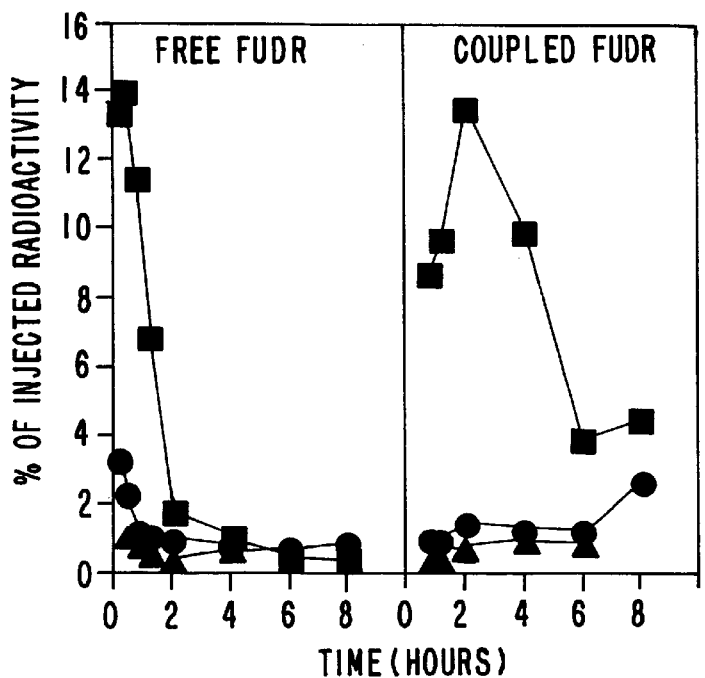
FIG. 7 shows the level of radioactivity in the liver, intestine and heart of mice after administration of the free and conjugated [$^3$H]FUDR.
Figure 8:
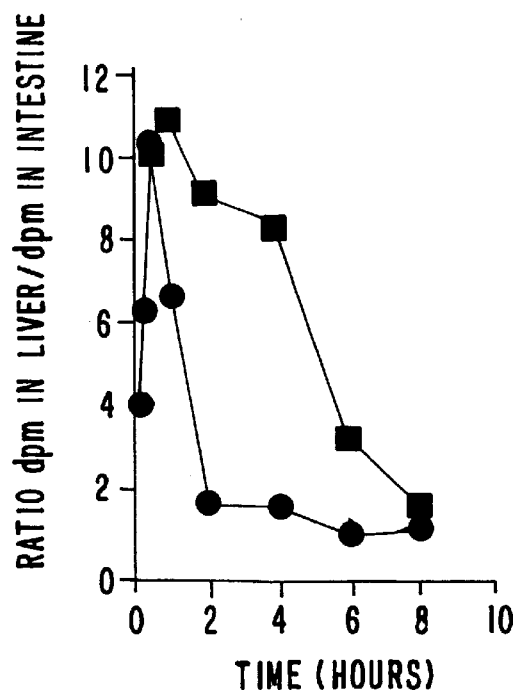
FIGS. 8 and 9 show the ratios of dpm in liver versus dpm in intestine and dpm in liver versus dpm in heart in animals administered with the conjugate or with the free drug.
Figure 9:
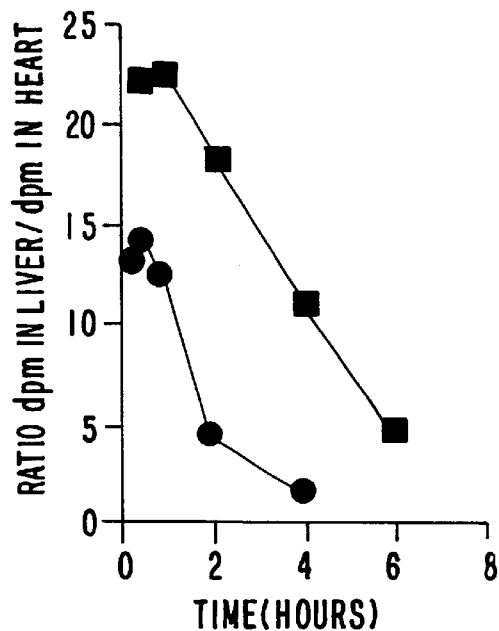

The levels of radioactivity in liver, intestine and heart of mice after administration of the free and conjugated [$^3$H] FUDR are reported in FIG. 7. FIGS. 8 and 9 show the ratios dpm in liver/dpm in intestine and dpm in liver/dpm in heart in animals administered with the conjugate or with the free drug. In mice treated with the conjugate the trapezoidal Areas Under Curve (AUC) of these ratios were 2.6 and 3.1 times higher than in animals receiving the free drug.

FIG. 7: Radioactivity in liver (■), intestine (●) and heart (▲) of mice injected with [$^3$H]FUDR (6 μg/g) and L-poly (LYS)-[$^3$H]FUDR (16.4 μg/g, equal to 6 μg/g [$^3$H]FUDR). Specific activity of both free and conjugated [$^3$H]FUDR was 32,000 dpm/μg. Each entry represents the mean value of results from 2 to 3 animals. Standard errors ranged from 1% to 4% of mean values.

FIG. 8: Ratios dpm in liver/dpm in intestine after administration of free (●) or conjugated (■) [$^3$H]FUDR. Ratios were obtained from data in FIG. 7. The AUCs (0–8 h) were 20.12 and 52.40 for the free and coupled drug, respectively.

FIG. 9: Ratios dpm in liver/dpm in heart after administration of free (●) or conjugated (■) [$^3$H]FUDR. Ratios were obtained from data of FIG. 7. Their AUCs were 26.13 and 80.91 for the free and the coupled drug, respectively.

B.2. Experiments with L-poly(LYS)dFdC

One milligram of this conjugate contained 351 μg of poly(LYS), 302 μg of lactose, and 347 μg of dFdCMP, corresponding to 262 μg of dFdC. Considering that 1 mg of poly(LYS) contains 7.8 μmol of lysine residues and that the molecular weights of lactose and dFdC are 342 and 247.2, respectively, it can be calculated that the ε-$NH_2$ groups of poly(LYS) were substituted by the sugar and by the drug at the percentage of 32 and 39, respectively.

When this conjugate was incubated at 37° C. for 4 hours in rat blood, only 1.7% of the drug was released (measured by HPLC).

Table 6 shows the effect of free and conjugated dFdC on Hep G2 cell proliferation. The $ID_{50}$s (doses producing a 50% inhibition of cell growth) were 1.11 and 2.13 ng/ml for the free and the conjugated drug, respectively. Inhibition by L-poly(LYS)-dFdC was rescued by asialofetuin, indicating that the conjugate entered Hep G2 cells through the ASGP-R.

TABLE 6

Effect of Free and Conjugated dFdC on Hep G2 Cell Proliferation

| Exp. | Compounds | Concentration ng/ml | Number of formed cells × $10^5$ |
|---|---|---|---|
| 1 | Control | | 2.42 ± 0.16 |
| | dFdC | 5.0 | 0 |
| | dFdC | 2.5 | 0 |
| | dFdC | 1.25 | 0.62 ± 0.06 |

TABLE 6-continued

Effect of Free and Conjugated dFdC on Hep G2 Cell Proliferation

| Exp. | Compounds | Concentration ng/ml | Number of formed cells × $10^5$ |
|---|---|---|---|
| | | | p = 0.009 |
| | dFdC | 0.6 | 2.30 ± 0.12 |
| 2 | Control | | 2.42 ± 0.16 |
| | L-Poly(LYS)-dFdC | 37.0 (10.0)[a] | 0 |
| | L-Poly(LYS)-dFdC | 18.5 (5.0) | 0 |
| | L-Poly(LYS)-dFdC | 9.3 (2.5) | 0.91 ± 0.12 |
| | | | p = 0.017 |
| | L-Poly(LYS)-dFdC | 4.6 (1.25) | 2.14 ± 0.53 |
| 3 | Control | | 5.22 ± 0.61 |
| | L-Poly(LYS)-dFdC | 18.5 (5.0) | 0 |
| | Asialofetuin | $10^6$ | 4.27 ± 0.18 NS[b] |
| | L-Poly(LYS)-dFdC + asialofetuin | 18.5 (5.0) $10^6$ | 3.71 ± 0.25 NS |

[a] The amounts of DFdC contained in the conjugates are shown in brackets.
[b] NS = not significant.

In conclusion, the experiments reported here demonstrate that the L-poly(LYS)-FUDR and the L-poly(LYS)-dFdC conjugates are pharmacologically active in vitro on HCC cells maintaining the asialoglycoprotein receptor. Furthermore, an enhanced accumulation of the drug was shown in liver versus intestine and heart in mice administered with the FUDR conjugate.

What is claimed is:

1. A conjugate of a basic polyamino acid with galactose or lactose residues and drug residues in which more than 50% of the side-chain amino groups of the basic polyamino acid are substituted with drug residues and with galactose or lactose residues wherein said drug residues are antitumoral nucleosides.

2. A conjugate, according to claim 1, wherein said basic polyamino acid is selected from the group consisting of poly-L-lysine and poly-L-ornithine.

3. A conjugate, according to claim 1, wherein said antitumoral drug is selected from the group consisting of 5-fluro-2'-deoxyuridine (FUDR) and 2'2'-difluorodeoxycytidine (dFdC).

4. A conjugate, according to claim 3, which is Lac-poly-L-lysine-FUDR.

5. A conjugate, according to claim 1, wherein the molar ratio of antitumoral drug residues to basic polyamino acid is higher than 30.

6. A conjugate, according to claim 5, wherein the molar ratio of antitumoral drug residues to basic polyamino acid is higher than 50.

7. A conjugate, according to claim 1, wherein the molar ratio of galactose or lactose residues to basic polyamino acid is greater than or equal to 5.

8. An antitumoral composition which contains as active ingredient antitumoral effective amount of a conjugate according to claim 1 in the presence of an acceptable carrier.

9. An antitumoral composition, according to claim 8, in a form suitable for parenteral, intravenous, subcantaneous or intramuscular administration.

10. A method of treating a hepatocarcinoma in a patient afflicted therewith comprising administering a composition according to claim 8 to said patient intramuscularly for a time and under conditions effective to inhibit hepatocarcinoma cell proliferation.

11. A method of treating a hepatocarcinoma in a patient afflicted therewith comprising administering a composition according to claim 8 to said patient subcutaneously for a time and under conditions effective to inhibit hepatocarcinoma cell proliferation.

12. A method of treating a hepatocarcinoma in a patient afflicted therewith comprising administering a composition according to claim 8 to said patient intravenously for a time and under conditions effective to inhibit hepatocarcinoma cell proliferation.

13. A method of treating a hepatocarcinoma in a patient afflicted therewith comprising administering a composition according to claim 8 to said patient parenterally for a time and under conditions effective to inhibit hepatocarcinoma cell proliferation.

14. An antitumoral composition which contains as active ingredient an antitumoral effective amount of a conjugate, according to claim 2, in the presence of an acceptable carrier.

15. An antitumoral composition which contains as active ingredient an antitumoral effective amount of a conjugate, according to claim 3, in the presence of an acceptable carrier.

16. An antitumoral composition which contains as active ingredient an antitumoral effective amount of a conjugate, according to claim 4, in the presence of an acceptable carrier.

17. An antitumoral composition which contains as active ingredient an antitumoral effective amount of a conjugate, according to claim 5, in the presence of an acceptable carrier.

18. An antitumoral composition which contains as active ingredient an antitumoral effective amount of a conjugate, according to claim 6, in the presence of an acceptable carrier.

19. An antitumoral composition which contains as active ingredient an antitumoral effective amount of a conjugate, according to claim 7, in the presence of an acceptable carier.

20. A conjugate according to claim 1 wherein the side-chain amino groups of the basic polyamino acid are substituted with lactose and the antitumoral drug is 5-fluoro-2'-deoxyuridine (FUDR).

21. A process of preparing a conjugate of a basic polyamino acid with galactose or lactose residues in which more than 50% of the side-chain amino groups of the base polyamino acid are substituted with drug residues and with galactose or lactose residues wherein said drug residues are antitumoral nucleosides, which comprises the steps of a) conjugating the basic polyamino acid with an antiviral drug, b) substituting the amino groups with lactose or galactose residues by means of reductive lactosamination with cyanoborohydride, and c) isolating the conjugate.

22. A process according to claim 21 wherein the drug conjugation is effected by means of the imidazolate of the drug and by performing the conjugation in a buffer medium at an alkaline pH.

23. A process according to claim 21 wherein the basic polyamino acid is selected from the group consisting of poly-L-lysine and poly-L-ornithine.

24. A process according to claim 22 wherein the basic polyamino acid is selected from the group consisting of poly-L-lysine and poly-L-ornithine.

25. A process according to claim 21 wherein said antitumoral drug is selected from the group consisting of 5-fluoro-2'-deoxyuridine (FUDR) and 2'2'-difluorodeoxycytidine (dFdC).

26. A process according to claim 22 wherein said antitumoral drug is selected from the group consisting of 5-fluoro-2'-deoxyuridine (FUDR) and 2'2'-difluorodeoxycytidine (dFdC).

27. A process according to claim 21 wherein the conjugate is Lac-poly-L-lysine-FUDR.

28. A process according to claim 22 wherein the conjugate is Lac-poly-L-lysine-FUDR.

29. A process according to claim 21 wherein the molar ratio of antitumoral drug residues to basic polyamino acid in the conjugate is higher than 30.

30. A process according to claim 21 wherein the molar ratio of antitumoral drug residues to polyamino acid in the conjugate is higher than 50.

31. A process according to claim 21 wherein the molar ratio of galactose or lactose residues to polyamino acid in the conjugate is greater than or equal to 5.

\* \* \* \* \*

UNITED STATES PATENT AND TRADEMARK OFFICE
CERTIFICATE OF CORRECTION

PATENT NO.     : 6,291,638 B1
DATED          : September 18, 2001
INVENTOR(S)    : Fiume et al.

It is certified that error appears in the above-identified patent and that said Letters Patent is hereby corrected as shown below:

<u>Title page,</u>
Item [73], the name of the assignee should read: -- Laboratori Baldacci S.p.a., Pisa (IT) -- instead of "Laboratori Balducci S.p.a., Pisa (IT)"

Signed and Sealed this

Eighteenth Day of June, 2002

*Attest:*

JAMES E. ROGAN
*Attesting Officer*           *Director of the United States Patent and Trademark Office*